US00PP15917P2

(12) United States Plant Patent
Kobayashi

(10) Patent No.: US PP15,917 P2
(45) Date of Patent: Aug. 9, 2005

(54) ***POINSETTIA* PLANT NAMED 'PER5499'**

(50) Latin Name: *Euphorbia pulcherrima*
Varietal Denomination: PER5499

(75) Inventor: Ruth Kobayashi, Carlsbad, CA (US)

(73) Assignee: Paul Ecke Ranch, Encinitas, CA (US)

( * ) Notice: Subject to any disclaimer, the term of this patent is extended or adjusted under 35 U.S.C. 154(b) by 7 days.

(21) Appl. No.: 10/955,476

(22) Filed: Sep. 30, 2004

(51) Int. Cl.[7] ..... A01H 5/00
(52) U.S. Cl. ..... Plt./303
(58) Field of Search ..... Plt./303

(56) References Cited

U.S. PATENT DOCUMENTS

PP7,308 P * 8/1990 Fruehwirth ..... Plt./303
PP8,771 P * 6/1994 Fruehwirth ..... Plt./303
PP12,636 P2 * 5/2002 Fruehwirth ..... Plt./303
PP12,921 P2 * 9/2002 Fruehwirth ..... Plt./303
PP13,326 P2 * 12/2002 Fruehwirth ..... Plt./303
2002/0112265 P1 * 8/2002 Fruehwirth ..... Plt./303

* cited by examiner

*Primary Examiner*—Anne Marie Grunberg
*Assistant Examiner*—W. C. Haas
(74) *Attorney, Agent, or Firm*—C. A. Whealy

(57) ABSTRACT

A new and distinct cultivar of *Poinsettia* plant named 'PER5499', characterized by its inflorescences with red-colored flower bracts with white-colored random flecks; dark green-colored leaves; uniform, compact, upright and mounded plant habit; early season flowering; natural season flower maturity date is late November for plants grown in Encinitas, Calif.; and excellent post-production longevity.

1 Drawing Sheet

Botanical designation: *Euphorbia pulcherrima* Willd.
Variety denomination: 'PER5499'.

CROSS-REFERENCE TO RELATED APPLICATIONS

The present application is co-pending with U.S. Plant patent application Ser. No. 10/955,482, filed Sep. 30, 2004, titled: "*Poinsettia* Plant Named 'PER6401'".

BACKGROUND OF THE INVENTION

The present Invention relates to a new and distinct cultivar of *Poinsettia* plant, botanically known as *Euphorbia pulcherrima* Willd., and hereinafter referred to by the name 'PER5499'.

The new *Poinsettia* is a product of a planned breeding program conducted by the Inventor in Encinitas, Calif. The objective of the breeding program is to create new early flowering *Poinsettia* cultivars having strong stems, attractive flower bract coloration, uniform plant habit and excellent post-production longevity.

The new *Poinsettia* is a naturally-occurring branch mutation of the *Poinsettia* cultivar Eckaykin (U.S. Plant Pat. No. 13,326). The new *Poinsettia* was discovered and selected by the Inventor in a controlled environment in Encinitas, Calif. on Dec. 31, 2000. The new *Poinsettia* was selected on the basis its unique flower bract coloration.

Asexual reproduction of the new *Poinsettia* by terminal cuttings propagated in a controlled environment in Encinitas, Calif., since February, 2001, has shown that the unique features of this new *Poinsettia* are stable and reproduced true to type in successive generations of asexual reproduction.

BRIEF SUMMARY OF THE INVENTION

The following traits have been repeatedly observed and are determined to be the unique characteristics of 'PER5499'. These characteristics in combination distinguish 'PER5499' as a new and distinct cultivar:

1. Inflorescences with red-colored flower bracts with random white-colored flecks.
2. Dark green-colored leaves.
3. Uniform, compact, upright and mounded plant habit.
4. Early season flowering; natural season flower maturity date is late November for plants grown in Encinitas, Calif.
5. Excellent post-production longevity.

Plants of the new *Poinsettia* are most similar to plants of the parent, the cultivar Eckaykin. Plants of the new *Poinsettia* differ from plants of the cultivar Eckaykin primarily in flower bract color as plants of the cultivar Eckaykin have red-colored flower bracts with pink flecks.

Plants of the new *Poinsettia* can be compared to plants of the cultivar PER6401 (U.S. Plant patent application Ser. No. 10/955,482). Plants of the new *Poinsettia* and the cultivar PER6401 differ primarily in flower bract coloration.

Plants of the new *Poinsettia* can be compared to plants of the cultivar 127 (U.S. Plant Pat. No. 7,308). In side-by-side comparisons conducted in Encinitas, Calif., plants of the new *Poinsettia* differed from plants of the cultivar 127 in the following characteristics:

1. Plants of the new *Poinsettia* were more compact than and not as vigorous as plants of the cultivar 127.
2. Plants of the new *Poinsettia* flowered about two weeks earlier than plants of the cultivar 127.
3. Plants of the new *Poinsettia* and the cultivar 127 differed in flower bract coloration as plants of the cultivar 127 had red-colored flower bracts with pink flecks.

BRIEF DESCRIPTION OF THE PHOTOGRAPHS

The accompanying colored photographs illustrate the overall appearance of the new *Poinsettia*, showing the colors as true as it is reasonably possible to obtain in colored reproductions of this type. Colors in the photographs may differ slightly from the color values cited in the detailed botanical description which accurately describe the colors of the new *Poinsettia*.

The photograph at the top of the sheet comprises a side perspective view of a typical flowering plant of 'PER5499' grown in a container.

The photograph at the bottom of the sheet comprises a top perspective view of a typical plant of 'PER5499'.

DETAILED BOTANICAL DESCRIPTION

The new *Poinsettia* has not been observed under all possible environmental conditions. The phenotype may vary somewhat with variations in environment such as temperature, daylength and light intensity, without, however, any variance in genotype.

The aforementioned photographs, following observations and averaged measurements describe plants grown in Encinitas, Calif. during the autumn under commercial practice in a polycarbonate-covered greenhouse with day temperatures averaging about 29° C., night temperatures averaging about 19° C. and light levels about 4,000 foot-candles. Single plants were grown in 16.5-cm pots and pinched once. Plants were flowered under natural season short day/long night conditions. Plants were about 17 weeks from unrooted cuttings when the photographs and the detailed botanical description were taken.

In the following description, color references are made to The Royal Horticultural Society Colour Chart, 1995 Edition, except where general terms of ordinary dictionary significance are used.

Botanical classification: *Euphorbia pulcherrima* Willd. cultivar PER5499.

Parentage: Naturally-occurring branch mutation of the *Poinsettia* cultivar Eckaykin, disclosed in U.S. Plant Pat. No. 13,326.

Propagation:

*Type cutting.*—Terminal cuttings.

*Time to initiate roots.*—About 10 days at 20 to 22° C.

*Time to develop roots.*—About 28 days at 20 to 22° C.

*Root description.*—Thick, fibrous, freely-branching; white in color.

Plant description:

*Plant form.*—Inverted triangle; top of plant mounded.

*Growth habit.*—Upright, compact and uniform plant habit. Moderately vigorous.

*Plant height.*—About 28 cm.

*Plant diameter or spread.*—About 41 cm.

*Lateral branch description.*—Quantity: About seven lateral branches develop after pinching. Length: About 20 cm. Diameter: About 6 mm. Internode length: About 3 to 3.5 cm. Strength: Strong. Texture: Smooth; glabrous. Color: 146B.

*Foliage description.*—Arrangement: Alternate, single. Length: About 12.5 cm. Width: About 7.5 cm. Shape: Ovate. Apex: Acute to acuminate. Base: Obtuse. Margin: Entire with irregular shallow lobing. Venation pattern: Pinnate. Texture, upper surface: Glabrous, smooth. Texture, lower surface: Pubescent. Surface: Rugose. Aspect: Flat. Color: Developing and fully expanded foliage, upper surface: Darker than 147A. Developing and fully expanded foliage, lower surface: 147A. Venation, upper surface: 147B. Venation, lower surface: 147C. Petiole: Length: About 4.8 cm. Diameter: About 3 mm. Texture, upper and lower surfaces: Smooth; glabrous. Color: 183A.

Inflorescence description:

*Inflorescence type and habit.*—Inflorescences are compound corymbs of cyathia with colored flower bracts subtending the cyathia. One inflorescence per lateral branch. Flowers are not fragrant. Flowers persistent.

*Natural flowering season.*—Autumn/winter in Northern Hemisphere. Flower initiation and development is induced under long nyctoperiod conditions. Early season flowering, response time, about 8 weeks; natural season flower maturity date is late November for plants grown in Encinitas, Calif.

*Post-production longevity.*—Plants of the new *Poinsettia* maintain good substance and bract color for about four weeks under interior conditions.

*Inflorescence size.*—Diameter: About 29 cm. Height (depth): About 3.5 cm.

*Flower bracts.*—Quantity per inflorescence: About 25. Length, largest bracts: About 13 cm. Width, largest bracts: About 7.5 cm. Shape: Elliptic to ovate. Apex: Narrowly acute to acuminate. Base: Acute. Margin: Entire with irregular shallow lobing. Texture, upper and lower surfaces: Glabrous; velvety. Surface: Slightly rugose. Aspect: Flat to folded upright along midvein. Venation pattern: Pinnate. Color: Developing or transitional bracts, upper surface: Ground color, 45B; random flecks, 158A to 158B. Developing or transitional bracts, lower surface: Ground color, 46D; random flecks, 51D. Fully developed bracts, upper surface: Ground color, 45B; random flecks, 158B. Fully developed bracts, lower surface: Ground color, 46D; random flecks, 51D. Venation, upper and lower surfaces: Similar to flower bract color. Bract petiole: Length: About 1.5 to 2.5 cm. Diameter: About 2.5 mm. Texture, upper and lower surfaces: Smooth; glabrous. Color: 45A.

*Cyathia.*—Quantity per corymb: About 18. Diameter of cyathia cluster: About 3.5 cm by 4 cm. Length: About 8 mm. Width: About 5 mm. Shape: Ovoid. Color, immature: 144A. Color, mature: 144B to 144C. Peduncle: Length: About 2 mm. Diameter: About 2 mm. Strength: Strong. Aspect: Mostly upright. Texture: Smooth; glabrous. Color: 144B. Stamens: Quantity per cyathium: About five to ten. Anther shape: Oval. Anther length: Less than 1 mm. Anther color: 59A. Amount of pollen: Scarce. Pollen color: 12A. Pistils: None observed. Nectaries: Quantity per cyathium: About one or two. Size: About 3 mm by 4 mm. Color: 14A.

Disease/pest resistance: Resistance to pathogens and pests common to *Poinsettias* has not been observed on plants grown under commercial conditions.

It is claimed:

1. A new and distinct cultivar of *Poinsettia* plant named 'PER5499', as illustrated and described.

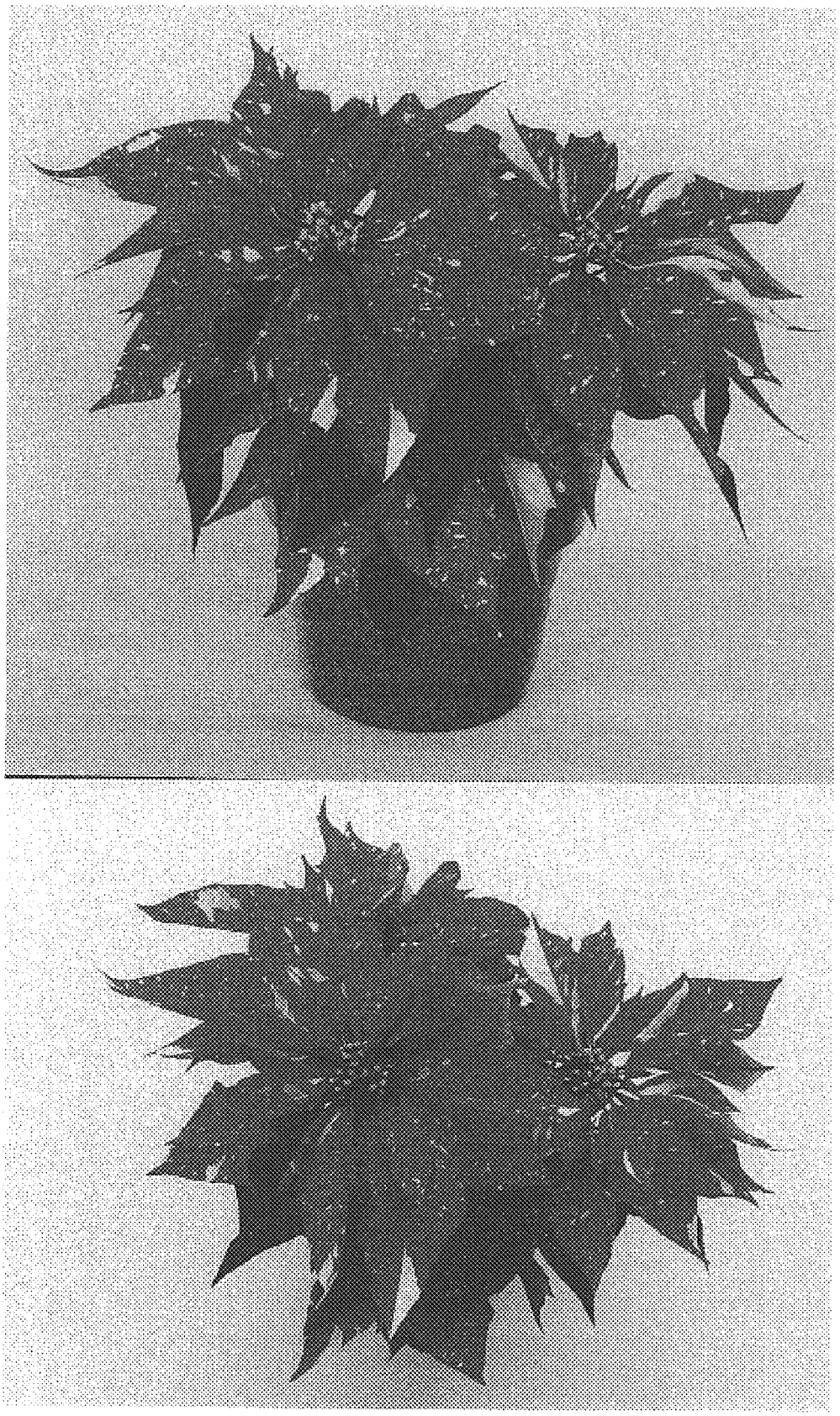

* * * * *